(12) United States Patent
Sommer et al.

(10) Patent No.: US 9,500,579 B1
(45) Date of Patent: Nov. 22, 2016

(54) SYSTEM AND METHOD FOR DETECTING COMPONENTS OF A MIXTURE INCLUDING TOOTH ELEMENTS FOR ALIGNMENT

(71) Applicant: Sandia Corporation, Albuquerque, NM (US)

(72) Inventors: Gregory Jon Sommer, Livermore, CA (US); Ulrich Y. Schaff, Livermore, CA (US)

(73) Assignee: Sandia Corporation, Albuquerque, NM (US)

( * ) Notice: Subject to any disclaimer, the term of this patent is extended or adjusted under 35 U.S.C. 154(b) by 381 days.

(21) Appl. No.: 14/256,294

(22) Filed: Apr. 18, 2014

Related U.S. Application Data

(60) Provisional application No. 61/818,360, filed on May 1, 2013.

(51) Int. Cl.
| | |
|---|---|
| *G01N 35/00* | (2006.01) |
| *G01N 21/00* | (2006.01) |
| *G01N 21/64* | (2006.01) |
| *G01N 21/59* | (2006.01) |

(52) U.S. Cl.
CPC .............. *G01N 21/00* (2013.01); *G01N 21/59* (2013.01); *G01N 21/64* (2013.01)

(58) Field of Classification Search
None
See application file for complete search history.

(56) References Cited

U.S. PATENT DOCUMENTS

| | | | |
|---|---|---|---|
| 3,555,284 A | 1/1971 | Anderson | |
| 3,744,974 A * | 7/1973 | Maddox et al. | 422/72 |
| 4,125,375 A | 11/1978 | Hunter | |
| 4,156,570 A | 5/1979 | Wardlaw | |
| 4,656,143 A | 4/1987 | Baker et al. | |
| 4,683,579 A | 7/1987 | Wardlaw | |
| 5,279,936 A | 1/1994 | Vorpahl | |
| 5,635,362 A | 6/1997 | Levine et al. | |
| 5,882,903 A | 3/1999 | Andrevski et al. | |
| 6,153,148 A | 11/2000 | Thomas | |
| 6,319,469 B1 | 11/2001 | Mian et al. | |
| 6,503,722 B1 | 1/2003 | Valkirs | |
| 6,887,384 B1 | 5/2005 | Frechet et al. | |
| 7,033,747 B2 | 4/2006 | Gordon | |
| 7,157,049 B2 | 1/2007 | Valencia et al. | |
| 7,332,326 B1 | 2/2008 | Kellogg et al. | |
| 7,758,810 B2 | 7/2010 | Lee et al. | |
| 2001/0055812 A1 | 12/2001 | Mian et al. | |
| 2002/0098535 A1 | 7/2002 | Wang et al. | |

(Continued)

FOREIGN PATENT DOCUMENTS

| | | |
|---|---|---|
| WO | WO-2008/143578 | 11/2008 |
| WO | WO 2009/098237 | 8/2009 |

OTHER PUBLICATIONS

Abi-Samra, Kameel et al., "Infrared controlled waxes for liquid handling and storage on a CD-microfluidic platform", The Royal Society of Chemistry; Lab on a Chip, 2011, 723-726.

(Continued)

*Primary Examiner* — Robert R Raevis
(74) *Attorney, Agent, or Firm* — Dorsey & Whitney, LLP

(57) ABSTRACT

Examples are described including assay platforms having tooth elements. An impinging element may sequentially engage tooth elements on the assay platform to sequentially align corresponding detection regions with a detection unit. In this manner, multiple measurements may be made of detection regions on the assay platform without necessarily requiring the starting and stopping of a motor.

30 Claims, 7 Drawing Sheets

(56) References Cited

U.S. PATENT DOCUMENTS

| | | | |
|---|---|---|---|
| 2002/0151043 A1 | 10/2002 | Gordon | |
| 2002/0164659 A1 | 11/2002 | Rao et al. | |
| 2003/0124719 A1 | 7/2003 | Woodside | |
| 2004/0072278 A1 | 4/2004 | Chou et al. | |
| 2005/0186685 A1 | 8/2005 | Kange et al. | |
| 2005/0215410 A1 | 9/2005 | Merino et al. | |
| 2005/0282220 A1 | 12/2005 | Prober et al. | |
| 2009/0004059 A1 | 1/2009 | Pugia et al. | |
| 2009/0325186 A1 | 12/2009 | Hinnah et al. | |
| 2010/0068754 A1 | 3/2010 | Kirakossian | |
| 2010/0120596 A1 | 5/2010 | Froman et al. | |
| 2010/0151560 A1 | 6/2010 | Wo et al. | |
| 2011/0045958 A1* | 2/2011 | Pedrazzini | 494/8 |
| 2014/0273241 A1* | 9/2014 | Ochranek et al. | 436/45 |

OTHER PUBLICATIONS

Ahanotu, et al., "*Staphylococcal enterotoxin* B as a Biological Weapon: Recognition, Management, and Surveillance of *Staphylococcal enterotoxin*", Applied Biosafety; vol. 11 (3), 2006, 120-126.

Albrecht, J.W. et al., "Micro Free-Flow IEF Enhanced by Active Cooling and Functionalized Gels", Electrophoresis, 2006, pp. 4960-4969, vol. 27.

Amersham, "Percoll: Methodology and Applications", 2001, 1-84.

Amukele, et al., "Ricin A-chain activity on stem-loop and unstructured DNA substrates.", Biochemistry; vol. 44(11), Mar. 25, 2005, 4416-4425.

Andersson, et al., "Parallel nanoliter microfluidic analysis system", Clinical Chemistry, 2007.

Baldwin, Robert L. , "How Hofmeister Ion Interactions Affect Protein Stability", Biophysical Journal; vol. 71, Oct. 1996, 2056-2063.

Berry, Scott M., "One-step Purification of Nucleic Acid for Gene Expression Analysis via Immiscible Filtration Assisted by Surface Tension", Lap Chip, May 21, 2011.

Boyko, Matthew et al., "Cell-Free DNA—a Marker to Predict Ischemic Brain Damage in a Rat Stroke Experimental Model", Journal of Neurosurg Anesthesiol, vol. 23, No. 3, Jul. 2011, 222-228.

Brigotti, et al., "Shiga toxin 1 acting on DNA in vitro is a heat-stable enzyme not requiring proteolytic activation", Biochimie Journal; 86(45), 2004, 305-309.

Carney, J. , "Rapid Diagnostic Tests Employing Latex Particles", Analytical Proceedings, Apr. 1990, 99-100.

Curtis, R. A. et al., "A Molecular approach to bioseparations: Protein-protein and protein-salt interactions", Chemical Engineering Science; vol. 61, 2006, 907-923.

Czeiger, David et al., "Measurement of Circulating Cell-Free DNA Levels by a New Simple Fluorescent Test in Patients With Primary Colorectal Cancer", Am J Clin Pathol, 2011, 264-270.

Endo, et al., "RNA N-Glycosidase Activity of Ricin A-chain. Mechanism of Action of the Toxic Lectin Ricin on Eukaryotic Ribosomes", The Journal of Biological Chemistry, vol. 262, No. 17, Jun. 15, 1987, 8128-8130.

Glorikian, Harry et al., "Smart-consumables product development: Implications for molecular disgnostics", DX Direction, 2010, 12-16.

Goldshtein, Hagit et al., "A Rapid Direct Fluorescent Assay for Cell-Free DNA Quantification in Biological Fluids", Annals of Clinical Biochemistry, 2009, 488-494.

Gorkin, et al., "Centrifugal microfluidics for biomedical applications", www.rsc.org/loc; Lab on a Chip, May 2010, 1758-1773.

Holmberg, et al., "Depurination of A4256 in 28 S rRNA by the Ribosome-inactivating Proteins from Barley and Ricin Results in Different Ribosome Conformations", Journal of Molecular Biology; vol. 259(1), May 31, 1996, 81-94.

Holmes, David et al., "Leukocyte analysis and differentiation using high speed microfluidic single cell impedance cytometry", Lab on a Chip 9, Aug. 7, 2009, 2881-2889.

Huang, et al., "The Primary Structure of *Staphylococcal enterotoxin* B. III. The Cyanogen Bromide Peptides of Reduced and Aminoethylated Enterotoxin B, and the Complete Amino Acid Sequence.", The Journal of Biological Chemistry vol. 245 No. 14, Jul. 25, 1970, 3518-3525.

Lee, et al., "Fully integrated lab-on-a-disc for simultaneous analysis of biochemistry and immunoassay from whole blood", Lab Chip, 2011.

Lee, B. S. et al., "A fully automated immunoassay from whole blood on a disc", Lab on a Chip 9, Mar. 5, 2009, 1548-1555.

Lim, C. T. et al., "Bead-based microfluidic immunoassays: The next generation", Biosensors Bioelectronics 22, Jul. 20, 2006, 1197-1204.

Lo, C.T. et al., "Photopolyermerized Diffusion-Defined Polyacrylamide Gradient Gels for On-Chip Protein Sizing", The royal Society of Chemistry, Lab on a Chip, vol. 8, No. 8, 2008, pp. 1273-1279.

Lo, Y. M. D. et al., "Plasma DNA as a Prognostic Marker in Trauma Patients", Clinical Chemistry 46:3, 2000, 319-323.

Madou, Marc et al., "LAB on a CD", Annual Rev. Biomed Eng 8, May 2006, 601-628.

Maes, Melissa L. et al., "Comparison of Sample Fixation and the use of LDS-751 or anti-CD45 or Leukocyte Identification in Mouse Whole Blood for Flow Cytometry", Journal of Immunological Methods, 319(1-2) Jan. 30, 2007, 79-86.

Min, Junhong et al., "Functional Integration of DNA Purification and Concentration Into a Real Time Micro-PCR Chip", The Royal Society of Chemistry; Lab on a Chip, 2011, 259-265.

Price, Christopher P. et al., "Light-Scattering Immunoassay", Principles and Practice of Immunoassay (Second Edition); Chapter 18, 1997, 445-480.

Rhodes, Andrew et al., "Plasma DNA concentration as a predictor of mortality and sepsis in critically ill patients", Critical Care, 2006, 1-7.

Rider, Todd H. et al., "A B Cell-Based Sensor for Rapid Identification of Pathogens", www.sciencemag.org; Science Volume. 301, Jul. 11, 2003, 213-215.

Riegger, L. et al., "Read-out concepts for multiplexed bead-based fluorescence immunoassays on centrifugal microfluidic platforms", Sensors and Actuators A-Physical, 2006, 455-462.

Saukkonen, et al., "Cell-Free Plasma DNA as a Predictor of Outcome in Severe Sepsis and Septic Shock", Clinical Chemistry; vol. 54:6, 2008, 1000-1007.

Schaff, et al., "Whole Blood Immunoassay Based on Centrifugal Bead Sedimentation", Clinical Chemistry Automation and Analytical Techniques 57:5, 2011, 753-761.

Schembri, et al., "Portable Simultaneous Multiple Analyte Whole-Blood Analyzer for Point-of-Care Testing", Clinical Chemistry 38/9, 1992, 1665-1670.

Schneider, et al., "Characterization of EBV-Genome Negative "Null" and "T" Cell Lines Derived From Children With Acute Lymphoblastic Leukemia and Leukemic Transformed Non-Hodgkin Lymphoma", International Journal of Cancer; 19(5), May 15, 1977, 621-626.

Yu, et al., "Bioinformatic processing to identify single nucleotide polymorphism that potentially affect Ape1 function.", Mutation Research/Genetic Toxicology and Environmental Mutagenesis; vol. 722(2), Jun. 17, 2011, 140-146.

Zhang, L. et al., "A New Biodosimetric Method: Branched Dna-Based Quantitative Detection of B1 Dna in Mouse Plasma", The British Journal of Radiology, vol. 83, Aug. 2010, 694-701.

Ziegler, Annemarie et al., "Circulating DNA: a new diagnostic gold mine?", Cancer Treatment Reviews, vol. 28, 2002, 255-271.

Churchill et al., "Detection of Listeria monocytogenes and the toxin listeriolysin O in food", Journal of Microbiological Methods, 2006; 64:141-170.

McBain et al., Polyethyleneimine functionalized iron oxide nanoparticles as agents for DNA delivery and transfection, Journal of Materials Chemistry, 17, pp. 2561-2565, available online Apr. 13, 2007.

Riahi et al. Analytical Chemistry. 2011. 83(16): 6349-6354 and Supporting Information.

(56) References Cited

OTHER PUBLICATIONS

Melting Temperature Calculation. Retrieved on asf from the internet: http://www.biophp.org/minitools/melting_temperature/demo.php?primer=CGT+TAC+CCG+CAG&basic-1&NearestNeighbor=1&cp=200&cs=50&cmg=0, Jul. 2015.

Berlier et al. The Journal of Histochemistry and Cytochemistry. 2003. 51(12): 1699-1712.

PubChem Search results for "2,3-dihydroxypropyl octanoate". Retrieved on Oct. 5, 2016 from the internet: https://www.hcbi.nim.nih.gov/pccompound/?term=2%2C3-dihydroxypropyl+octanoate. (4 pp.).

PubChem entry for TWEEN 20. Retrieved on Oct. 4, 2016 from the internet: https://pubchem.ncbi.nlm.nih.gov/compound/Tween_20#section=Names-and-identifiers. (2 pp.).

Sigma-Aldrich product page for TWEEN 20 archived from Jun. 28, 2012. Retrieved on Oct. 5, 2016 from the internet: https://web.archive.org/web/20120628080753/http://www.sigmaaldrich.com/catalog.product/sial/p1379?ang=en&region=. (43 pp.).

* cited by examiner

SYSTEM AND METHOD FOR DETECTING COMPONENTS OF A MIXTURE INCLUDING TOOTH ELEMENTS FOR ALIGNMENT

CROSS-REFERENCE TO RELATED APPLICATION

This application claims benefit under 35 U.S.C. 119(e) to U.S. provisional patent application Ser. No. 61/818,360, entitled "SYSTEM AND METHOD FOR CONTROLLING DISK ROTATION FOR BIOASSAY" filed May 1, 2013, which provisional application is incorporated herein by reference in its entirety for any purpose.

STATEMENT REGARDING RESEARCH & DEVELOPMENT

This invention was developed under Contract DE-AC04-94AL85000 between Sandia Corporation and the U.S. Department of Energy. The U.S. Government has certain rights in the invention.

TECHNICAL FIELD

Embodiments of the invention relate generally to measurement systems and examples include methods, systems and apparatus employing motors and locking mechanisms for conducting measurements, including the detection and/or quantification of components in a mixture. Examples of microfluidic disks including tooth elements are described. The tooth elements may in some examples aid in aligning an assay region with a detection unit.

BACKGROUND

Automated measurement of samples is important in a number of industries, such as the chemical and biotechnology industries, where the concentration of certain components of the sample is of interest. For example, quantification of biomolecules such as proteins and nucleic acids from patient samples is an important area of research and commercial development. Quantification of biomolecules and other types of samples is typically performed by optical measurements including fluorescence, luminescence, or relative light absorption. Portable solutions for these applications are a large and growing segment of the overall market.

Measurement systems typically shift a platform containing the sample to bring the sample in alignment with an optical detection unit, or vice versa. This may be achieved by either stopping the sample when in alignment with the optical detection unit and conducting the measurement, or synchronizing light detection with an actively moving sample. Synchronized detection may be cumbersome at high speeds, and typically requires positional sensors on the platform and a high quality motor with feedback mechanisms to maintain a constant shifting speed. Additionally, the time at which the optics are in alignment with the detection region is very brief, requiring a high intensity signal to achieve a favorable signal to noise ratio. Therefore, synchronized detection is typically reserved for high cost or low sensitivity systems.

DETAILED DESCRIPTION

Certain details are set forth below to provide a sufficient understanding of embodiments of the invention. However, it will be clear to one skilled in the art that embodiments of the invention may be practiced without various of these particular details. In some instances, well-known chemical structures, chemical components, molecules, materials, electronic components, circuits, control signals, timing protocols, and software operations have not been shown in detail in order to avoid unnecessarily obscuring the described embodiments of the invention.

Disclosed herein are example embodiments of systems, apparatuses and methods for detecting and/or quantifying one or more components of a sample. Examples are described that include tooth elements for alignment of an assay region with a detection unit. As mentioned above, existing systems and methods for performing an assay may be cumbersome or offer limited sensitivity. Therefore, there may be a need for systems and methods to perform an assay quickly, accurately, and at a relatively low cost.

For example, stopping a sample at increments during optical, or other detection, measurement may be advantageous because of longer integration time for light or other signal collection, which may increase the signal to noise ratio and hence sensitivity. Accordingly, rather than continuously presenting different detection regions of samples to a detection unit, it may be desirable to present one region to the detection unit, stop for a measurement time, then present a next region of sample to the detection unit. However, the measurement system may need to allow multiple stops with high precision to ensure proper alignment between the sample and the detection unit. Stepper motors have been used to achieve multiple stops with high precision, but may be prohibitively costly to implement in some examples because of the cost of the stepper motor along with feedback sensors and driver circuitry to ensure proper alignment. Alignment precision may be limited to the minimum step size of the stepper motor and driver circuitry. Additionally, there may be a tradeoff between maximum spin rate of the stepper motor and the minimum step size. Therefore, stepper motors may not be well suited to systems that require low cost components or high speed sample processing.

Figure 1:
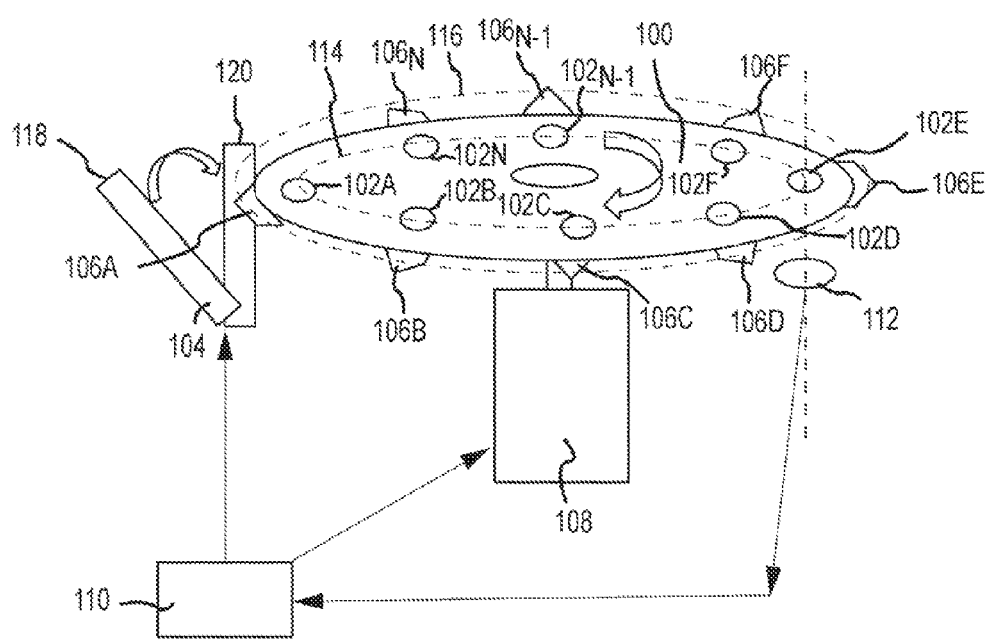
FIG. 1 is a schematic illustration of a measurement system arranged in accordance with embodiments of the present invention.

FIG. 1 is a schematic illustration of a measurement system including an assay platform 100, detection regions 102A-102N, tooth elements 106A-106N, a motor 108, an impinging element 104, a controller 110, and a detection unit 112, according to some examples. The assay platform 100 may be a substrate that includes multiple detection regions 102A-102N and corresponding tooth elements 106A-106N. The assay platform 100 may be implemented in generally any shape, for example circular (see, e.g., FIGS. 1-4) or rectangular (see, e.g., FIG. 5). It should be understood that the assay platform 100 may be formed in other shapes.

The assay platform 100 may be formed from a variety of materials, such as metals, glasses, polymers, and combinations thereof. The assay platform 100 may be formed by known manufacturing methods, including, but not limited to, microfluidic manufacturing techniques, semiconductor manufacturing techniques. Techniques such as injection molding, cutting, or both, may be used. The assay platform 100 may be disposable in some examples. The assay platform 100 may be portable in some examples.

The assay platform 100 may be fabricated with detection regions 102A-102N positioned on its surface. The detection regions 102A-102N may be areas, such as chambers, reservoirs, or other openings in the platform, configured to house samples. In some examples, the detection regions 102A-102N may be narrower on their peripheral end in order to concentrate a component of a sample, as will be described below. The detection regions 102A-102N may be positioned at a fixed distance from one another. A fixed distance may allow for proper alignment between the detection regions 102A-102N and the detection unit 112. The detection regions 102A-102N may move along a first path 114 when driven by the motor 108.

The assay platform 100 may generally include any microfluidic components desirable or useful for conducting an assay including, but not limited to, inlet port(s), outlet port(s), channels, chambers, reservoirs, pumps, valves, mixers, vents, and the like. Multiple assays may generally be performed on one assay platform 100, with a detection portion of the assay taking place at the detection regions 102A-102N. Examples of assay platforms and systems which may be usable with the tooth elements and alignment techniques described herein include systems and assay platforms described in U.S. patent application Ser. No. 12/891, 977 and Ser. No. 13/423,008, which applications are incorporated herein by reference in their entirety for any purpose.

Tooth elements 106A-106N may be provided on the periphery of the assay platform 100, for example along the circumference of a circularly-shaped assay platform 100. In some examples, the tooth elements 106A-106N may be provided on a surface of the assay platform 100 such that the tooth elements 106A-106N protrude in a direction perpendicular to the plane of the assay platform 100. The tooth elements 106A-106N may be formed separately and coupled (e.g. adhered or bonded) to the assay platform 100, or may be formed along with the assay platform 100 in a unitary structure (e.g. through cutting or injection molding). The tooth elements 106A-106N may be formed by any known manufacturing method, for example molding, thermoforming, cutting, or combinations thereof. One tooth element 106A-106N may be provided for each of the detection regions 102A-102N in some examples. Generally, the tooth elements 106A-106N are provided such that once movement of the assay platform 100 is stopped by engaging a tooth element 106A-106N, a corresponding detection region 102A-102N is in alignment with a detection unit. In some examples, one tooth element 106A-106N may be associated with multiple detection regions and either bring the multiple detection regions into alignment with corresponding multiple detection units or may bring a single detection region into alignment with a detection unit and the detection unit may be moved to also access another detection region during the stopped time period. In some examples, tooth elements 106A-106N may be placed adjacent (e.g. peripheral to in the case of circular disk embodiments) to the detection regions 102A-102N. Adjacent placement may facilitate proper alignment of the detection regions 102A-102N with the detection unit 112 when the assay platform is stopped by engaging the tooth element. The tooth elements 102A-102N may move along a second path 116 when the motor 108 is moving the assay platform 100.

The tooth elements 106A-106N may be shaped to engage with the impinging element 104. In some examples, the assay platform 100 may stop moving when one or more of the tooth elements 106A-106N engages with the impinging element 104. For example, the assay platform 100 in some examples may be spun to rotate each detection region of the assay platform past a detection unit. In some examples, spinning the assay platform 100 may also be used to facilitate performance of the assay (e.g. by centrifugal force, examples of which are described in co-pending applications listed above, for example). The tooth elements 106A-106N may be positioned such that one side of each tooth element 106A-106N is aligned with one of the detection regions 102A-102N. Thus, when the impinging element 104 engages with each tooth element 106A-106N, the corresponding detection region 102A-102N may be in a desired alignment, such as within a measurement area of the detection unit 112. For example, the detection unit 112 may be aligned with the impinging element 104 so that a measurement area of the detection unit may be aligned with the detection region 102A-102N that corresponds to the tooth element 106A-106N that is engaged with the impinging element 104. In some examples, the detection unit 112 may be placed in another position so that its measurement area aligns with a different detection region 102A-102N than the detection region 102A-102N corresponding to the tooth element 106A-106N engaged with the impinging element 104.

The impinging element 104 may include a movable structure configured to allow for movement of the assay platform when placed in a first position 118 and engage at least one tooth element 106A-106N when placed in a second position 120. The impinging element 104 may be communicatively coupled (e.g. electrically) to the controller 110. The controller 110 may provide a control signal to the impinging element 104 to place the impinging element in the first or the second position 120. In this manner, the controller 110 may provide a control signal to move the impinging element 104 to sequentially engage with each tooth element of the multiple tooth elements 106A-106N. The impinging element 104 may be shaped to securely engage with the tooth elements 106A-106N. For example, the impinging element 104 may have a flat surface that engages with a flat surface of the tooth elements 106A-106N. The impinging element 104 may have a complimentary feature as that of the tooth elements 106A-106N in some examples.

The detection unit 112 may perform measurements to detect and/or quantify an analyte in any or all of the detection regions present on the assay platform. The detection unit 112 may, for example, include an optical light sensor for performing optical measurements, such as fluorescence, luminescence, and/or relative light absorption. In some examples, other sensors (e.g. electrical sensors) may be included additionally or instead in the detection unit 112 to support other detection methodologies. The detection unit 112 may be mounted in a system in proximity to a mount for holding the assay platform 100. Generally, the detection unit 112 is positioned in a system such that when the impinging element 104 is engaged with one or more of the tooth elements 106A-106N, a corresponding detection region is aligned with the detection unit 112 such that detection unit 112 is positioned to take a measurement from the detection region, or to move in a known manner to the detection region. A mount may be provided in a system for receiving the assay platform which may generally be inserted into and removed from the system. The detection unit 112 may accordingly be positioned in a known manner relative to the mount to facilitate alignment between detection regions on platforms that may be placed on the mount and the detection unit 112.

Figure 2:
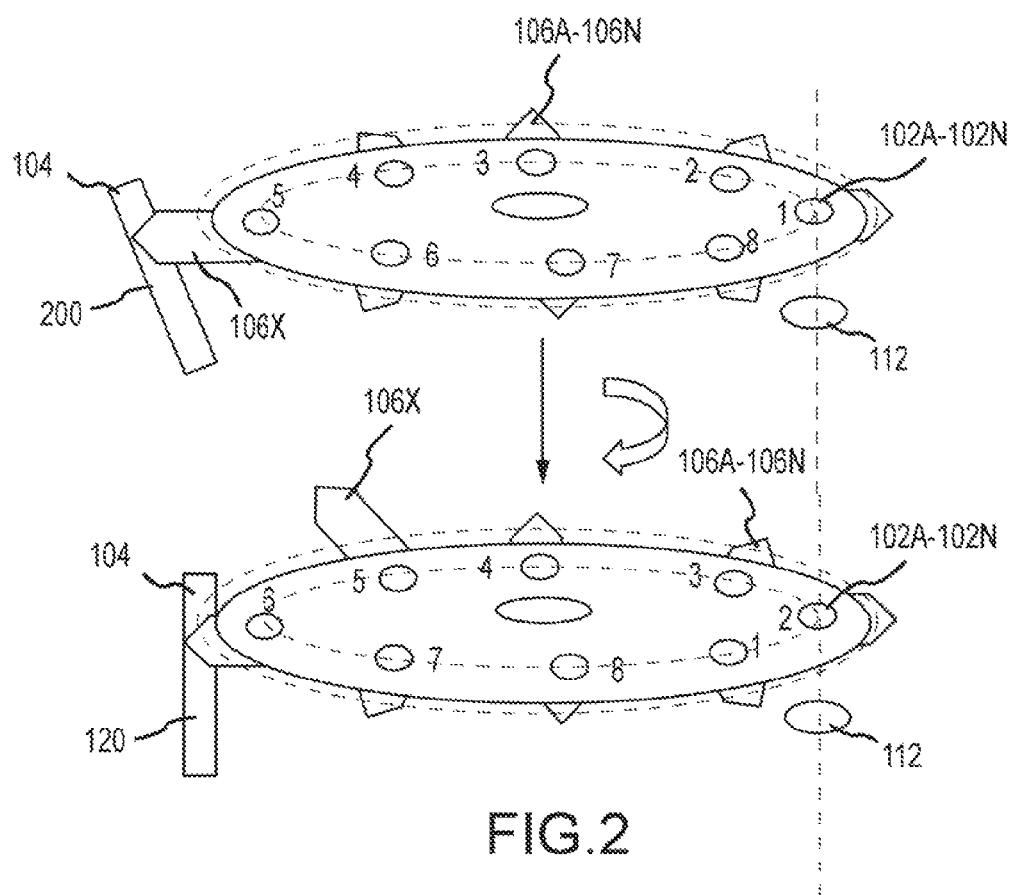
FIG. 2 is a schematic illustration of an assay platform including multiple tooth elements and an extended tooth element, according to examples of the present invention.
Figure 3:
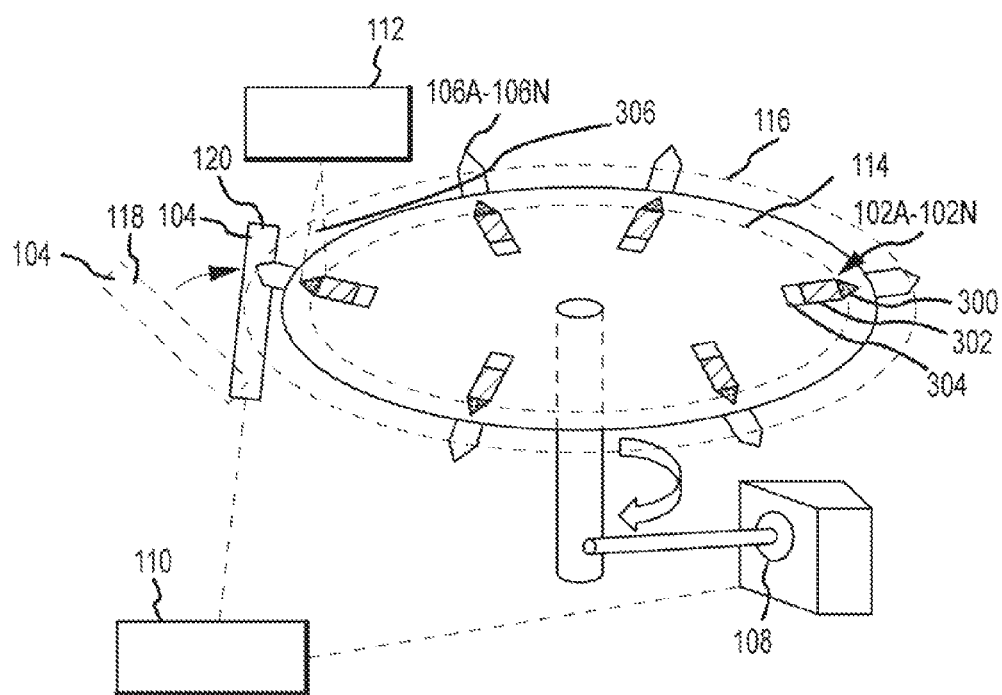
FIG. 3 is a schematic illustration of a measurement system in accordance with examples of the present invention.
Figure 4:
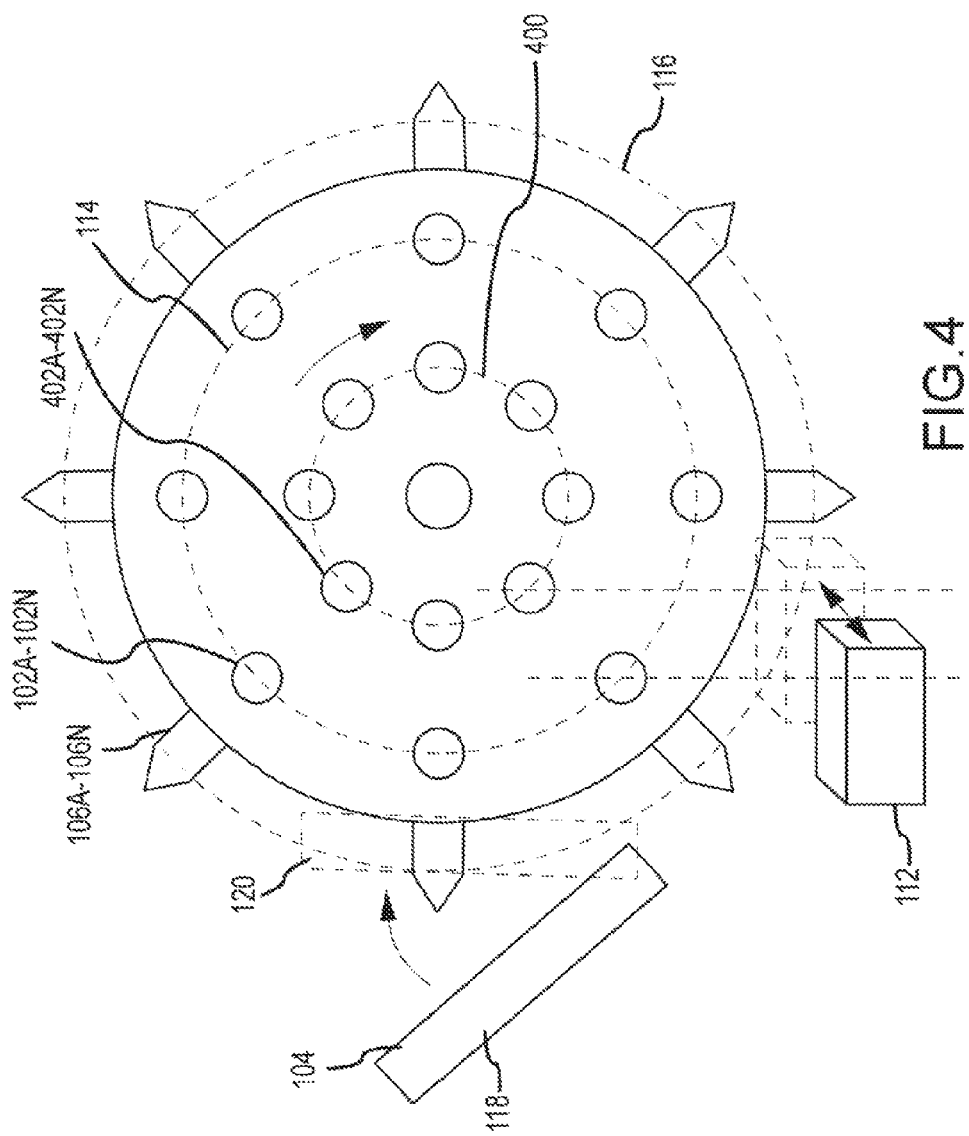
FIG. 4 is a schematic illustration of another assay platform arranged in accordance with examples of the present invention.
Figure 5:
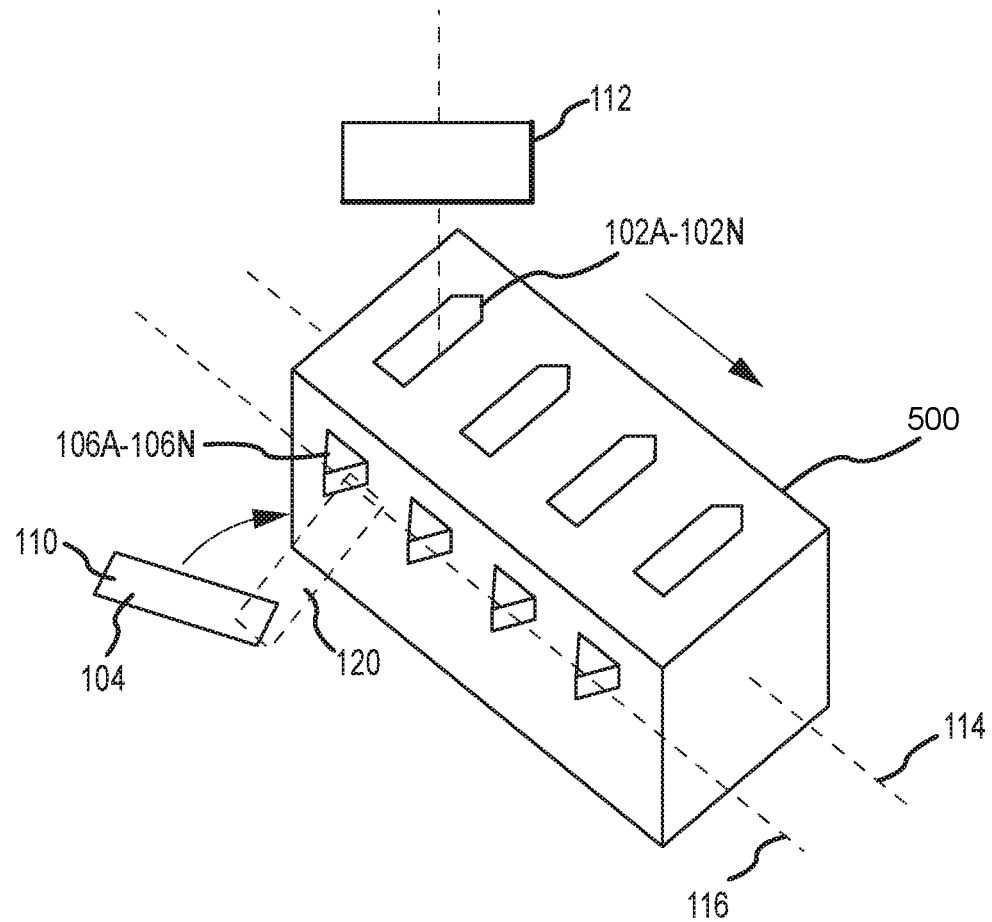
FIG. 5 is a schematic illustration of another assay platform configured to move along a linear path, according to examples of the present invention.

In some examples, the detection unit 112 may take a measurement when the impinging element 104 is engaged with one or more of the tooth elements 106A-106N, thereby preventing or restricting the assay platform 100 from moving. It may be advantageous to take a measurement while the assay platform 100 is not moving in order to increase the integration time for light (or other signal) collection, which may increase the signal to noise ratio and hence sensitivity. The detection unit 112 may be positioned such that when the impinging element 104 is in the second position 120, the detection unit 112 is aligned with at least one of the multiple detection regions 102A-102N. The optical sensor of the detection unit 112 may be oriented towards the detection regions 102A-102N. In some examples, as shown in FIGS. 1-2, the detection unit 112 may be mounted below the assay platform 100 and oriented upwards. In some examples, as shown in FIGS. 3-5, the detection unit 112 may be mounted above the assay platform 100 and oriented downwards.

It may be advantageous to identify the detection region from which each measurement was taken. In some examples, identification may be performed by manually observing which assay region was measured during one or more time intervals. However, it may be desirable to have another mechanism to identify which assay region corresponds with a particular measurement made by the detection unit. In some examples, barcodes or other identifying structures may be placed on the assay platform and may be read or recognized to associate a measurement made by the detection unit with a particular assay region.

FIG. 2 is a schematic illustration of an assay platform 100 including multiple tooth elements 106A-106N and an extended tooth element 106X, according to some examples. The extended tooth element 106X may facilitate identification of a starting point for measurements taken by the detection unit 112. The extended tooth element 106X may be positioned on the periphery of the assay platform 100. The extended tooth element 106X may be formed separately and coupled to the assay platform 100, or may be formed along with the with the assay platform 100 in a unitary structure. The extended tooth element 106X may have different dimensions than the multiple tooth elements 106A-106N. For example, the extended tooth element 106X may be longer than the multiple tooth elements 106A-106N. The extended tooth element 106X may correspond to one of the multiple detection regions 102A-102N.

The impinging element 104 may be configured for placement in a third position 200, in which the impinging element 104 may engage with the extended tooth element 106X. It may be advantageous to place the impinging element 104 in the third position 200 for measurements of individual samples placed in a predefined order in the detection regions 102A-102N. For example, the extended tooth element 106X may define a start point for sequential measurement of the multiple detection regions 102A-102N. In this example, the impinging element 104 may be set to the third position 200, and the assay platform 100 may be moved by the motor 108 until the impinging element 104 engages with the extended tooth element 106X. In this manner, it may be known that a first measurement taken by the detection unit 112 corresponds with the detection region 102A-102N associated with the extended tooth element 106X. The impinging element 104 may shift back and forth from the first position 118 to the second position 120 to sequentially stop the assay platform 100 so that each detection region 102A-102N then aligns with the measurement area of the detection unit 112. In this manner, measurements of samples placed in a predefined order in the detection regions 102A-102N may be taken and subsequently identified. Using the extended tooth element 106X to define the start point of the assay may avoid the need for a barcode or other mechanism for defining the start point, thereby reducing costs in some examples.

In an alternate embodiment, two solenoid motors may be used to implement the impinging element 104. That is, instead of a physical impinging element protruding from the assay platform, multiple solenoids may be employed for positioning. It may be advantageous in some examples to use two solenoid motors instead of other types of motors to reduce costs. In this embodiment, each solenoid motor may be positioned proximate to the assay platform 100 and oriented such that a solenoid associated with the motor may extend towards the multiple tooth elements 106A-106N and/or the extended tooth element 106X. When a first solenoid extends out, it may engage with the extended tooth element 106X to prevent movement of the assay platform 100 and define a start point of the assay. When a second solenoid extends out, it may sequentially engage with the multiple tooth elements 106A-106N.

FIG. 3 is a schematic illustration of a measurement system including a motor 108 configured to apply a centrifugal force to multiple detection regions 102A-102N of an assay platform 100, according to embodiments described herein. The motor 108 may be a DC motor coupled to the assay platform 100. In contrast to conventional implementations of automated quantification systems, the motor 108 may be implemented using a brushed DC motor, instead of a brushless motor, such as a stepper motor. A number of known types of motors may be used, such as a solenoid motor, a servo motor, a linear actuator, or combinations thereof. A motor other than a stepper motor may be used to perform automated measurements because the tooth elements 106A-106N may engage with the impinging element 104 at precise positions to ensure proper alignment between the detection regions 102A-102N and the measurement area of the detection unit 112. Therefore, it may not be necessary for the motor 108 itself to have a precise stopping mechanism. Additionally, positional sensors may not be necessary due to the positional precision provided by the impinging element 104 and tooth element 106A-106N mechanism. Thus, costs may be reduced in some examples by using a motor other than a stepper motor, avoiding the need for positional sensors, or both.

In some examples, the motor 108 may apply a centrifugal force to an assay platform mounted in the system. Centrifugal force may be used to separate one or more components of one or more samples positioned within one or more of the multiple detection regions 102A-102N of the assay platform 100. For example, components of biological and clinical samples may need to be separated to facilitate measurement (e.g. detection and/or quantification) of an analyte. Applying a centrifugal force may achieve a separation of one or more components of the biological or clinical samples placed within one or more of the multiple detection regions 102A-102N. In some examples, a fluid sample positioned within one or more of the multiple detection regions 102A-102N may include a plurality of beads 300 having complexes formed thereon, in which individual ones of the complexes include a target analyte and a labeling agent bound to the beads 300 in cooperation with the target analyte. The fluid sample may also include free labeling agent 304 that may be unbound. The motor 108 may apply a centrifugal force to the fluid sample, whereby the beads 300 in the fluid sample may be transported responsive to the centrifugal force through a density media 302 to pellet out at the detection region 102A-102N. Free labeling agent 304 may have insufficient density to be transported through the density media 302 and may not be present at the detection region 102A-102N. It should be understood that the motor 108 may be configured to move the assay platform 100 to effect a separation of a variety of different types of mixtures placed in the multiple detection regions 102A-102N responsive to a centrifugal force. Examples of assays usable with examples of the present invention are described in the applications incorporated by reference above.

In some examples, the controller 110 may be communicatively coupled (e.g. electrically) to the motor 108. The controller 110 may be an electronic device, for example a computing device, that may transmit control signals at predefined times and/or predefined intervals to recipient devices. Additionally, the controller 110 may store timing information using a timing device, for example a timer integrated circuit. The control signals may be transmitted using an implementation of a protocol recognizable by the recipient devices. The recipient device may include the detection unit 112, the impinging element 104, and/or the motor 108. The controller 110 may receive user input that defines parameters of the measurement system, such as distance between each of the detection regions 102A-102N, rotational speed, etc. The controller 110 may provide control signals to the impinging element 104 to place the impinging element 104 in the first position 118, second position 120, third position 200 (in some examples), fourth position (in some examples), or combinations thereof. By placing the impinging element 104 in the second position 120, a tooth element 106A-106N on the assay platform 100 may be engaged, and the assay platform 100 may be stopped. Accordingly, following placement of the impinging element 104 in the second position 120 after a predetermined period of time, the controller 110 may provide control signals to the detection unit 112 to make a measurement. Following a measurement time the controller 110 may provide control signals to the impinging element 104 to place the impinging element in the first position 118, allowing the motor to move the assay platform 100 again. After a predetermined time, the controller 110 may again provide control signals to place the impinging element 104 in the second position 120. The predetermined time may be set such that the impinging element 104 is moved into the second position 120 in time to stop the assay platform such that a next detection region 102A-102N is aligned with the detection unit 112. In this manner, the controller 110 may provide control signals such that the impinging element 104 engages with each tooth element 106A-106N. The controller 110 may send control signals to the motor 108 to start and stop the motor 108. In some examples, the controller 110 may stop the motor 108 for a predetermined interval after the impinging element 104 engages with each tooth element 106A-106N. In some examples, the assay platform 100 is stopped when the impinging element 104 engaged with any of the tooth elements 106A-106N, and a measurement may be performed by the detection unit 108. It may be advantageous to stop the motor 108 when the assay platform 100 is stopped in order to reduce electrical noise originating from the active motor during analysis by the detection unit 108.

The motor 108 may move the assay platform 100 such that the multiple detection regions 102A-102N move along a first path 114 and the multiple tooth elements 106A-106N move along a second path 116. In some examples, the first path 114 and the second path 116 may be circular (see, e.g., FIGS. 1-4). In some examples, the first path 114 and the second path 116 may be linear (see, e.g., FIG. 5). As described above, the impinging element 104 may move back and forth between a first position 118 and a second position 120. When in the second position 120, the impinging element may cross the second path 116, thereby engaging with one or more of the multiple tooth elements 106A-106N. The detection unit 112 may be positioned such that its measurement area includes a portion of the first path, thereby allowing for measurements to be taken when any of the multiple detection regions 102A-102N are positioned at the portion of the first path overlapping with the measurement area of the detection unit 112.

FIG. 4 is a schematic illustration of an assay platform 100 including two sets of detection regions 102A-102N and 402A-402N and a detection unit 112 configured to move to align with each set, in some examples. The first set of detection region 106A-106N may move along a first path 114 and the second set of detection may move along a third path 400. Both the first set of detection regions 102A-102N and the second set of detection regions 402A-402N may have corresponding tooth elements 106A-106N. Each tooth element 106A-106N may correspond to a detection region of both the first set of detection regions 102A-102N and the second set of detection regions 402A-402N. In some examples, both the first path 114 and the third path 400 are circular, in which the first path 114 has a larger radius than the third path 400. In this manner, the detection regions in each set may be positioned at a same radius from a center of the substrate. It may be advantageous to have multiple sets of detection regions in order to maximize or increase the number of samples that may be placed on an assay platform 100. It should be understood that any number of sets of detection regions may be included on the assay platform 100.

In some examples, the detection unit 112 may align with different portions of the detection regions 102A-102N. It may be advantageous to move the detection unit 112 such that the measurement area of the detection unit 112 is directed to a particular portion of the detection regions 102A-102N when components of interest in a sample are manipulated to be positioned in the particular portion. For example, when a centrifugal force is applied to detection regions 102A-102N in a circular assay platform 100, the denser components may be transported to the peripheral end of the assay platform 100 while the less dense components will be more towards the center of the assay platform 100. Thus, if a measurement of the denser components is desired, then the detection unit 112 may be aligned with the peripheral end of the detection regions 102A-102N. Alternatively, if a measurement of the less dense components is desired, then the detection unit 112 may be aligned with the end of the detection regions 102A-102N closest to the center of the assay platform 100.

FIG. 5 is a schematic illustration of an assay platform 500 that may move along a linear path, according to some examples. A linear path may be preferable when centrifugation is not necessary to perform the assay, for example. The assay platform 100 may be rectangular in shape and may include multiple detection regions 102A-102N positioned along a linear path, as shown in FIG. 5. The detection unit 112 may be placed proximate to the assay platform 100, and may be oriented such that the optical light sensor of the detection unit 112 is directed towards an area through which the multiple detection regions 102A-102N may be passed. As described above, the assay platform 100 may include multiple tooth elements 106A-106N that are positioned on the periphery of the assay platform 100, and may correspond to the multiple detection regions 102A-102N. For a rectangular assay platform 100, the multiple tooth elements 106A-106N may be placed on one side or two sides of the assay platform 100. If the multiple tooth elements 106A-106N are only on one side, then one impinging element 104 may be used to sequentially engage each tooth element 106A-106N. However, if the multiple tooth elements (not shown) are on two sides, then two impinging elements (not shown) may be used to sequentially engage the tooth elements. In this embodiment, the two impinging elements may synchronously engage the two tooth elements that correspond to each detection region 102A-102N.

Figure 6:
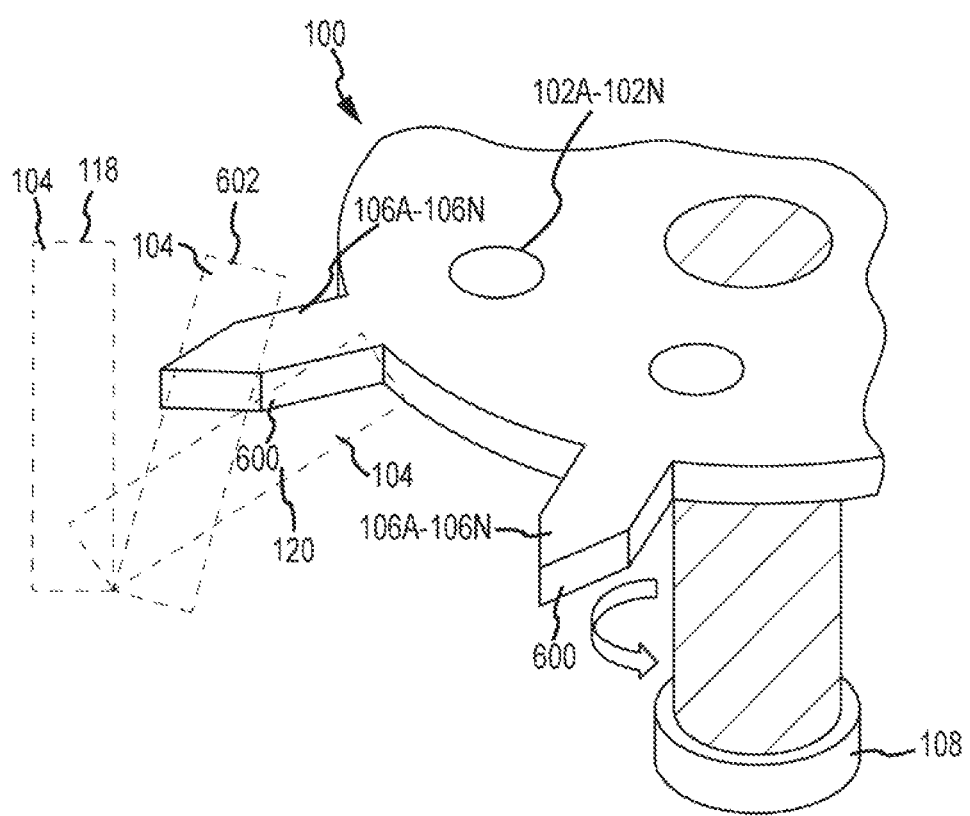
FIG. 6 is a schematic illustration of another assay platform arranged in accordance with examples of the present invention.

FIG. 6 is a schematic illustration of an assay platform 100 including multiple tooth elements 106A-106N including an angular portion 600. In some examples, the impinging element 104 may be configured for placement in a fourth position 602, in which the impinging element 104 may partially engage with the tooth elements 106A-106N. Partial engagement between the impinging element 104 and the tooth elements 106A-106N may allow for movement of the assay platform 100 to be restricted to only in one direction. This may be achieved by shaping the tooth elements 106A-106N in a manner so that the motor is partially frustrated by the impinging element 104 when moving in a first direction and fully frustrated by the impinging element 104 when moving in a second direction. In some examples, the second direction may be the opposite direction relative to the first direction. When partially frustrated, the motor 108 may be able to overcome the resistance from the partial engagement between the impinging element 104 and the tooth elements 106A-106N to move the assay platform 100 such that the next detection region 102A-102N may align with the detection unit 112.

In some examples, a first side of each of the tooth elements 106A-106N may include an angular portion 600 to partially frustrate the motor 108 in a first direction (see, e.g., FIG. 6). The angular portion 600 may be on the peripheral end of each tooth element 106A-106N, whereby the impinging element 104 placed in the fourth position 602 may partially engage with the angular portion 600. The geometry of the angular portion 600 may provide a path for the impinging element 104 to move peripherally, thereby passing to the next tooth element. A second side of each of the tooth elements 106A-106N may not include the angular portion 600, which may fully frustrate the motor 108 in a second direction. The second side of the tooth elements 106A-106N may be flat, thereby fully engaging with the impinging element 104 placed in the fourth position. Thus, the impinging element 104 in the fourth position 602 may allow for unidirectional movement of the assay platform 100.

Figure 7:
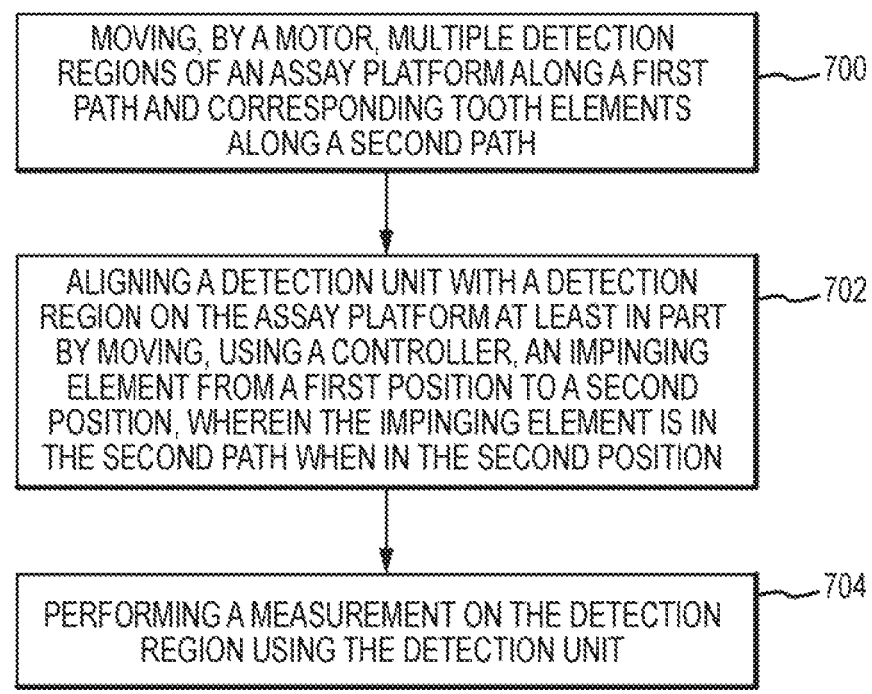
FIG. 7 is a flowchart depicting a method for performing an assay, according to examples of the present invention.

FIG. 7 is a flowchart depicting a method for performing an assay, according to embodiments described herein. Operation 700 involves moving, by a motor, multiple detection regions (e.g. 102A-102N of FIG. 1) of an assay platform along a first path (e.g. 114 of FIG. 1) and corresponding tooth elements (e.g. 106A-106N of FIG. 1) along a second path (e.g. 116 of FIG. 1). Operation 702 involves aligning a detection unit with a detection region on the assay platform at least in part by moving, using a controller, an impinging element from a first position to a second position. The impinging element is in the second path when in the second position. Accordingly, the impinging element may serially engage with multiple ones of the tooth elements (e.g. 106A-106N of FIG. 1) for a predetermined interval at each tooth element. Moving the assay platform may apply a centrifugal force to a sample placed within one or more of the detection regions, whereby components of the sample may separate responsive to the centrifugal force.

Operation 704 involves performing a measurement on the detection region using the detection unit. The measurement may be performed during the predetermined interval where the impinging element is engaged with multiple ones of the tooth elements. For example, the measurement may detect fluorescence present in the detection region, which may allow identification of analyte including, but not limited to biomolecules such as proteins, nucleic acids, or combinations thereof. The method of FIG. 7 may be implemented using any of the structures shown in FIGS. 1-5 in some examples.

From the foregoing it will be appreciated that, although specific embodiments of the invention have been described herein for purposes of illustration, various modifications may be made without deviating from the spirit and scope of the invention.

What is claimed is:

1. An assay system comprising:
    an assay platform comprising multiple detection regions and corresponding tooth elements;
    a motor coupled to the assay platform, wherein the motor is configured to move the assay platform such that the detection regions move along a first path and the tooth elements move along a second path;
    an impinging element configured for placement in a first position that allows for movement of the assay platform and a second position, wherein the impinging element engages at least one tooth element when in the second position;
    a detection unit configured to detect an analyte, wherein the detection unit is positioned such that when the impinging element is in the second position, the detection unit is aligned with at least one of the multiple detection regions; and
    a controller communicatively coupled to the impinging element and the motor, wherein the controller is configured to provide a control signal to the impinging element to place the impinging element in the first position or the second position.

2. The assay system of claim 1, wherein the assay platform comprises a circular substrate defining multiple tooth elements along a circumference of the circular substrate.

3. The assay system of claim 1, wherein at least one of the multiple detection regions corresponds to an extended tooth element having a different dimension than others of the tooth elements.

4. The assay system of claim 3, wherein the impinging element is further configured for placement in a third position, in which the impinging element engages the extended tooth element.

5. The assay system of claim 1, wherein the controller is configured to move the impinging element to sequentially engage with each tooth element of the tooth elements.

6. The assay system of claim 5, wherein the controller is further configured to stop the motor for a predetermined interval after the impinging element engages with each tooth element.

7. The assay system of claim 1, wherein the detection region is configured to contain any of a biological and a clinical sample.

8. The assay system of claim 1, wherein the detection unit includes an optical light sensor.

9. The assay system of claim 1, wherein the detection regions configured to move along a first path are a first set of detection regions, and wherein the assay platform further comprises a second set of detection regions, the second set of detection regions configured to move along a third path, wherein the detection unit is configured to shift from a position associated with the first path to a position associated with the second path.

10. The assay system of claim 1, wherein the assay platform comprises a substrate formed from an injection molded polymer.

11. The assay system of claim 1, wherein the controller is configured to stop the motor while the detection unit performs a measurement of at least one detection region.

12. The assay system of claim 1, wherein the motor is a brushed DC motor.

13. The assay system of claim 1, wherein the first and second paths are circular.

14. The assay system of claim 13, wherein the motor is configured to move the assay platform to effect a separation of one or more mixtures placed in the detection regions responsive to a centrifugal force.

15. The assay system of claim 14, wherein the mixture is a fluid sample, wherein the fluid sample includes a plurality of beads having complexes formed thereon, individual ones of the complexes comprising a target analyte and a labeling agent, wherein the fluid sample further includes a free labeling agent, and wherein the beads in the fluid sample are transported responsive to the centrifugal force.

16. A method for performing an assay, the method comprising:
   moving, by a motor, multiple detection regions of an assay platform along a first path and corresponding tooth elements along a second path;
   aligning a detection unit with a detection region on the assay platform at least in part by moving, using a controller, an impinging element from a first position and a second position, wherein the impinging element is in the second path when in the second position; and
   performing a measurement on the detection region using the detection unit.

17. The method of claim 16 further comprising serially engaging the impinging element with multiple ones of the tooth elements for a predetermined interval at each tooth element.

18. The method of claim 17, wherein the measurement is performed during the predetermined interval.

19. The method of claim 16, wherein the assay platform comprises a circular substrate defining multiple tooth elements along a circumference of the circular substrate.

20. The method of claim 19, wherein the first path is circular.

21. The method of claim 20 wherein moving the detection regions applies a centrifugal force to one or more mixtures in the detection regions.

22. The method of claim 21, wherein the centrifugal force effects a separation of one or more components of the mixtures.

23. The assay system of claim 22, wherein the mixture is a fluid sample, wherein the fluid sample includes a plurality of beads having complexes formed thereon, individual ones of the complexes comprising a target analyte and a labeling agent, wherein the fluid sample further includes a free labeling agent, and wherein the beads in the fluid sample are transported responsive to the centrifugal force.

24. The method of claim 16 further comprising moving a second set of detection regions of the assay platform along a third path, wherein the detection unit is configured to shift from a position associated with the first path to a position associated with the second path, and wherein the detection regions configured to move along a first path are a first set of detection regions.

25. An assay platform comprising:
   a substrate at least partially defining multiple detection regions, the multiple detection regions positioned at a same radium from a center of the substrate;
   a first tooth element extending a first distance away from a center of the substrate, wherein the first tooth element is associated with one of the plurality of detection regions; and
   multiple second tooth elements, each multiple second tooth element associated with a remaining one of the multiple detection regions, wherein the multiple second tooth elements extend a second distance away from the center of the substrate, and wherein the first distance is larger than the second distance.

26. The assay platform of claim 25, wherein the multiple detection regions are configured to move along a first path.

27. The assay platform of claim 26, wherein the first path is circular.

28. The assay platform of claim 27 wherein moving the detection regions applies a centrifugal force to one or more mixtures in the detection regions.

29. The assay platform of claim 28, wherein the centrifugal force effects a separation of one or more components of the mixtures.

30. The assay platform of claim 29, wherein the mixture is a fluid sample, wherein the fluid sample includes a plurality of beads having complexes formed thereon, individual ones of the complexes comprising a target analyte and a labeling agent, wherein the fluid sample further includes a free labeling agent, and wherein the beads in the fluid sample are transported responsive to the centrifugal force.

* * * * *